United States Patent

(12) United States Patent
Tsujikawa

(10) Patent No.: US 11,992,317 B2
(45) Date of Patent: May 28, 2024

(54) ALERTNESS ESTIMATION APPARATUS, ALERTNESS ESTIMATION METHOD, AND COMPUTER-READABLE RECORDING MEDIUM

(71) Applicant: NEC Corporation, Tokyo (JP)

(72) Inventor: Masanori Tsujikawa, Tokyo (JP)

(73) Assignee: NEC CORPORATION, Tokyo (JP)

(*) Notice: Subject to any disclaimer, the term of this patent is extended or adjusted under 35 U.S.C. 154(b) by 285 days.

(21) Appl. No.: 17/425,840

(22) PCT Filed: Feb. 1, 2019

(86) PCT No.: PCT/JP2019/003752
§ 371 (c)(1),
(2) Date: Jul. 26, 2021

(87) PCT Pub. No.: WO2020/157989
PCT Pub. Date: Aug. 6, 2020

(65) Prior Publication Data
US 2022/0313132 A1 Oct. 6, 2022

(51) Int. Cl.
G08B 23/00 (2006.01)
A61B 5/00 (2006.01)
(Continued)

(52) U.S. Cl.
CPC ............ A61B 5/18 (2013.01); A61B 5/4809 (2013.01); A61B 5/7203 (2013.01);
(Continued)

(58) Field of Classification Search
CPC ....... A61B 5/18; A61B 5/4809; A61B 5/7203; A61B 5/7267; G06V 40/171; G06V 10/60; G06V 10/62; G06V 40/18
(Continued)

(56) References Cited

U.S. PATENT DOCUMENTS 5,859,921 A * 1/1999 Suzuki ................ G06V 40/168
382/257
6,717,518 B1 * 4/2004 Pirim ........................ B60R 1/12
340/576
(Continued)

FOREIGN PATENT DOCUMENTS

JP 2007-257043 A 10/2007
JP 2009-018091 A 1/2009
(Continued)

OTHER PUBLICATIONS

International Search Report for PCT Application No. PCT/JP2019/003752, dated Apr. 23, 2019.
(Continued)

Primary Examiner — Naomi J Small

(57) ABSTRACT

An alertness estimation apparatus 10, includes: an image extraction unit 11 that extracts an image of a portion including eyes from an image data of a face image of a human; a first alertness estimation unit 12 that estimates a first alertness based on the extracted image; a pulse wave detection unit 13 that determines whether or not the estimated first alertness satisfies a set condition, and detect a pulse wave of the human from the face image, when the first alertness satisfies the set condition; and a second alertness estimation unit 14 that estimates a second alertness of the human based on the detected pulse wave.

14 Claims, 6 Drawing Sheets

(51) Int. Cl.
*A61B 5/18* (2006.01)
*G06V 10/60* (2022.01)
*G06V 10/62* (2022.01)
*G06V 10/82* (2022.01)
*G06V 40/16* (2022.01)
*G06V 40/18* (2022.01)

(52) U.S. Cl.
CPC ............ *A61B 5/7267* (2013.01); *G06V 10/60* (2022.01); *G06V 10/62* (2022.01); *G06V 10/82* (2022.01); *G06V 40/171* (2022.01); *G06V 40/18* (2022.01)

(58) Field of Classification Search
USPC ......................................................... 340/575
See application file for complete search history.

(56) References Cited

U.S. PATENT DOCUMENTS

| | | | | |
|---|---|---|---|---|
| 10,467,488 | B2* | 11/2019 | Sicconi | G06V 40/20 |
| 2008/0037837 | A1* | 2/2008 | Noguchi | G10L 15/25 |
| | | | | 382/118 |
| 2010/0090839 | A1* | 4/2010 | Omi | B60K 28/04 |
| | | | | 340/576 |
| 2011/0216181 | A1* | 9/2011 | Yoda | A61B 5/18 |
| | | | | 348/78 |
| 2014/0210978 | A1* | 7/2014 | Gunaratne | A61B 5/18 |
| | | | | 348/77 |
| 2016/0120477 | A1* | 5/2016 | Takahashi | A61B 5/681 |
| | | | | 600/500 |
| 2016/0374606 | A1 | 12/2016 | Shikii et al. | |
| 2017/0020432 | A1 | 1/2017 | Kusukame et al. | |
| 2017/0325750 | A1* | 11/2017 | Tanabe | A61B 5/7278 |
| 2018/0116597 | A1* | 5/2018 | Yu | A61B 5/0064 |
| 2018/0176741 | A1* | 6/2018 | Cremer | G06F 16/9535 |
| 2018/0202823 | A1* | 7/2018 | Maekawa | G06V 10/56 |
| 2018/0279892 | A1* | 10/2018 | Qi | A61B 5/7214 |
| 2019/0227547 | A1* | 7/2019 | Sugahara | B60W 50/0098 |

FOREIGN PATENT DOCUMENTS

| | | |
|---|---|---|
| JP | 2009-028239 A | 2/2009 |
| JP | 2012-164040 A | 8/2012 |
| JP | 2013-081708 A | 5/2013 |
| JP | 2017-012730 A | 1/2017 |
| JP | 2017-164526 A | 9/2017 |

OTHER PUBLICATIONS

English translation of Written opinion for PCT Application No. PCT/JP2019/003752, dated Apr. 23, 2019.

* cited by examiner

Fig.2

| SIGNAL OF A PULSE WAVE AT TIME T | SIGNAL OF A PULSE WAVE AT TIME T... | SIGNAL OF A PULSE WAVE AT TIME T+N | WAKEFULNESS (SECOND ALERTNESS) |
|---|---|---|---|
| 0.1 | ... | 0.8 | 0 (SLEEPING) |
| 0.2 | ... | 0.4 | 1 (AWAKE) |
| 0.5 | ... | 0.7 | 0 (SLEEPING) |
| 1.0 | ... | 0.2 | 1 (AWAKE) |
| 0.9 | ... | 0.1 | 1 (AWAKE) |
| ... | ... | ... | ... |

Fig.5

| SIGNAL OF A PULSE WAVE AT TIME T | SIGNAL OF A PULSE WAVE AT TIME T··· | SIGNAL OF A PULSE WAVE AT TIME T+N | WAKEFULNESS (SECOND ALERTNESS) |
|---|---|---|---|
| 0.1 | ... | 0.8 | 0 (NON-REM SLEEP) |
| 0.2 | ... | 0.4 | 1 (AWAKE) |
| 0.5 | ... | 0.7 | 0.5 (REM SLEEP) |
| 1.0 | ... | 0.2 | 1 (AWAKE) |
| 0.9 | ... | 0.1 | 1 (AWAKE) |
| ... | ... | ... | ... |

ALERTNESS ESTIMATION APPARATUS, ALERTNESS ESTIMATION METHOD, AND COMPUTER-READABLE RECORDING MEDIUM

This application is a National Stage Entry of PCT/JP2019/003752 filed on Feb. 1, 2019, the contents of all of which are incorporated herein by reference, in their entirety.

TECHNICAL FIELD

The present invention relates to an alertness estimation apparatus and an alertness estimation method for estimating an alertness of human, and further relates to a computer-readable recording medium in which a program for executing these apparatus and method is recorded.

BACKGROUND ART

In recent years, the working-age population has decreased due to the declining birthrate and aging population, and the labor shortage is progressing. Under such circumstances, attempts to replace some of the work that humans have done up to now with robots or AI (Artificial Intelligence) are increasing. However, among the jobs performed by humans, it is difficult to replace them with robots or AI for jobs that require intellectual labor. For this reason, it will be essential for humans to maintain and improve the productivity of intellectual labor in the future.

By the way, unlike machines, humans feel drowsy during work (become a state of low arousal) due to lack of sleep or hangover The cause of lack of sleep is a disease such as sleep apnea syndrome. Naturally, in such a situation, it becomes difficult for the worker to maintain normal productivity.

It is assumed that the wakefulness of the worker is detected and the detected wakefulness is presented to the worker, thereby causing the worker to think about the cause of lack of sleep and to give an opportunity to review the lifestyle. According to this, it may be possible to suppress a decrease in an alertness of the worker during work. Therefore, it is important to accurately detect the wakefulness of humans.

For example, Patent Document 1 discloses an apparatus for detecting a wakefulness of a human. Specifically, the apparatus disclosed in Patent Document 1 measures the blinking time from a face image, and further measures the heart rate variability from a heart rate sensor. Then, the apparatus disclosed in Patent Document 1 determines that the human is a sign of falling asleep when the measured blink time is extended and the start of increase in the HF component is observed in the measured heart rate variability.

LIST OF RELATED ART DOCUMENTS

Patent Document

Patent Document 1: Japanese Patent Laid-Open Publication No. 2009-18091

SUMMARY OF INVENTION

Problems to be Solved by the Invention

By the way, according to the apparatus disclosed in Patent Document 1, it is possible to detect a wakefulness of humans, but for that purpose, it is necessary to equip each human with a sensor for detecting a heart rate. As a result, there is a problem that the cost is too high for the apparatus disclosed in Patent Document 1 to be introduced by a company or the like.

On the other hand, it is considered that the above problem can be solved by introducing a technique for detecting a heart rate from a face image of a human into the apparatus disclosed in Patent Document 1. However, in this case, in addition to the process of measuring the blinking time from the face image, the apparatus needs to constantly perform the process of detecting the heart rate from the face image, which increases the processing load on the apparatus. Further, since the apparatus disclosed in Patent Document 1 is realized by a computer used by employees or the like in business or a computer prepared for another purpose, increasing the processing load is a problem that cannot be overlooked.

An example object of the present invention is to provide an alertness estimation apparatus, an alertness estimation method, and a computer-readable recording medium that solve the aforementioned problems and detect a wakefulness of human without increasing the introduction cost and processing load.

Means for Solving the Problems

To achieve the aforementioned example object, an alertness estimation apparatus according to an example aspect of the present invention includes:
- an image extraction unit that configured to extract an image of a portion including eyes from an image data of a face image of a human;
- a first alertness estimation unit that configured to estimate a first alertness based on the extracted image;
- a pulse wave detection unit that configured to determine whether or not the estimated first alertness satisfies a set condition, and detect a pulse wave of the human from the face image, when the first alertness satisfies the set condition; and
- a second alertness estimation unit that configured to estimate a second alertness of the human based on the detected pulse wave.

Furthermore, to achieve the aforementioned example object, an alertness estimation method according to an example aspect of the present invention includes:
- (a) a step of extracting an image of a portion including eyes from an image data of a face image of a human;
- (b) a step of estimating a first alertness based on the extracted image;
- (c) a step of determining whether or not the estimated first alertness satisfies a set condition, and detecting a pulse wave of the human from the face image, when the first alertness satisfies the set condition; and
- (d) a step of estimating a second alertness of the human based on the detected pulse wave.

Moreover, to achieve the aforementioned example object, a computer-readable recording medium according to an example aspect of the present invention has recorded therein a program including instructions that causes a computer to execute:
- (a) a step of extracting an image of a portion including eyes from an image data of a face image of a human;
- (b) a step of estimating a first alertness based on the extracted image;
- (c) a step of determining whether or not the estimated first alertness satisfies a set condition, and detecting a pulse wave of the human from the face image, when the first alertness satisfies the set condition; and (d) a step of estimating a second alertness of the human based on the detected pulse wave.

Advantageous Effects of the Invention

As described above, according to the present invention, it is possible to detect a wakefulness of human without increasing the introduction cost and the processing load.

BRIEF DESCRIPTION OF THE DRAWINGS

FIG. 2 is a diagram showing an example of training data used for learning a neural network used by a second alertness estimation unit in the example embodiment of the present invention.

FIG. 5 is a diagram showing an example of training data used in the modified example 3 according to the example embodiment of the present invention.

EXAMPLE EMBODIMENT

Example Embodiment

The following describes an alertness estimation apparatus, an alertness estimation method, and a program according to an example embodiment of the present invention with reference to FIG. 1 to FIG. 6.

[Apparatus Configuration]

Figure 1:
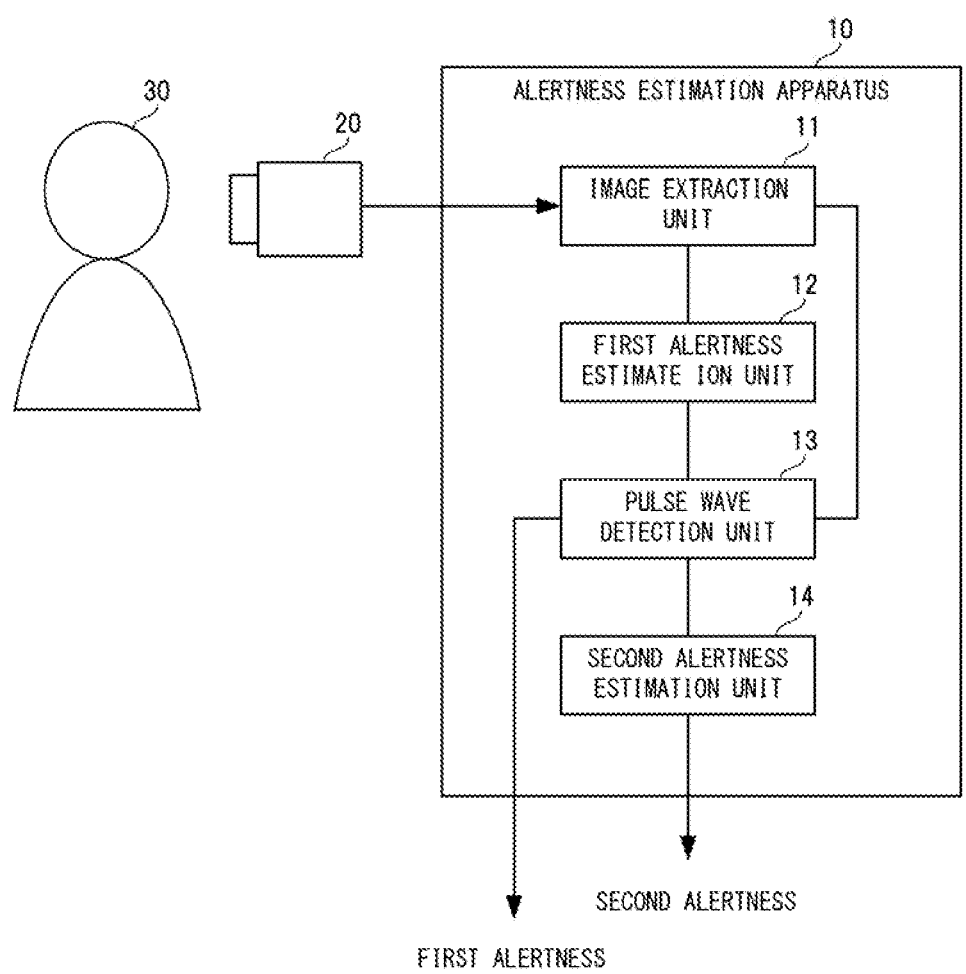
FIG. 1 is a block diagram showing a configuration of an alertness estimation apparatus according to an example embodiment of the present invention.

First, a configuration of the alertness estimation apparatus according to the present example embodiment will be described using FIG. 1. FIG. 1 is a block diagram showing a configuration of an alertness estimation apparatus according to an example embodiment of the present invention.

The alertness estimation apparatus 10 according to the present example embodiment shown in FIG. 1 is an apparatus that estimates the alertness of human 30. As shown in FIG. 1, the alertness estimation apparatus 10 includes an image extraction unit 11, a first alertness estimation unit 12, a pulse wave detection unit 13, and a second alertness estimation unit 14.

The image extraction unit 11 extracts an image of a portion including eyes from an image data of a face image of a human 30. The first alertness estimation unit 12 estimates a first alertness based on the extracted image. The pulse wave detection unit 13 determines whether or not the estimated first alertness satisfies a set condition, and detect a pulse wave of the human from the face image, when the first alertness satisfies the set condition. The second alertness estimation unit 14 estimates a second alertness of the human 30 based on the detected pulse wave.

As described above, in the present example embodiment, first, the pulse wave detection process from the face image and the alertness estimation process from the pulse wave are executed, only when the alertness estimated from the state of eyes portions satisfies the set condition. Therefore, an increase in the processing load of the apparatus is suppressed. Further, in the present example embodiment, it is not necessary for each human to wear a sensor in order to detect the pulse wave. Therefore, according to the present example embodiment, it is possible to detect the wakefulness of humans without increasing an introduction cost and the processing load.

Subsequently, the configuration of the alertness estimation apparatus 10 and the functions of each unit in the present example embodiment will be described more specifically.

As shown in FIG. 1, in the present example embodiment, the alertness estimation apparatus 10 is connected to the imaging apparatus 20. The imaging apparatus 20 is arranged so that the face of the human 30 who uses the alertness estimation apparatus can be photographed. The imaging apparatus 20 outputs the image data of the captured image (image including the face) to the alertness estimation apparatus 10 at set intervals. The imaging apparatus 20 is, for example, a digital camera, a web camera, or the like.

In the present example embodiment, the image extraction unit 11 first receives the image data output by the imaging apparatus 20, and extracts a feature value of the received image data each time. Subsequently, the image extraction unit 11 compares the extracted feature value with the feature value of eye and other facial parts registered in advance. The image extraction unit 11 specifies region of eyes and region around the eyes in the image data, and extracts an image of the specified region.

In the present example embodiment, the first alertness estimation unit 12 detects states (open or closed) of the eyelids from the image extracted by the image extraction unit 11 (hereinafter referred to as "extracted image"). The first alertness estimation unit1 2 determines whether or not the human 30 is awake according to the detected state, and sets the determination result as the first alertness. Therefore, the first alertness is either a value "1" indicating that the huma 30 is awake or a value "0" indicating that the human 30 is sleeping.

Specifically, the first alertness estimation unit 12 acquires the extracted images for the set period, and for each extracted image, calculates the degree of opening and closing of the eyelids in the extracted image (closed state 0.0 or open state 1.0). The first alertness estimation unit 12, for example, calculates the time when the eyelids are closed, based on time-series of the calculated the degree of opening and closing. Subsequently, the first alertness estimation unit 12 determines that the human 30 is awake in case that the time when the eyelids are closed is equal to or less than the threshold value. On the other hand, the first alertness estimation unit 12 determines that the human 30 is sleeping in case that the time when the eyelids are closed exceeds the threshold value.

Then, when the first alertness estimation unit 12 determines that the human 30 is awake, the first alertness estimation unit 12 sets the first alertness indicating that the human human 30 is awake to "1". Further, when the first alertness estimation unit 12 determines that the human 30 is sleeping the first alertness estimation unit 12 sets the first alertness indicating that the human 30 is sleeping to "0 (zero)".

When the first alertness estimation unit 12 determines that the human 30 is not awake, that is, when the first alertness is "0", the pulse wave detection unit 13 determines that the first alertness satisfies the set condition. Then, the pulse wave detection unit 13 detects the pulse wave of the human 30 from the face image taken by the imaging apparatus 20. In the present embodiment, the pulse wave is detected by detecting a change in the brightness (G value) of the green component in the face image. This technique takes advantage of the property that hemoglobin absorbs green light.

Specifically, the pulse wave detection unit 13 calculates the average value of the brightness values of the extracted green components of all the pixels in the image for each output image data for the set period. Then, the brain wave detection unit 13 acquires the time-series change of the brightness value of the green component by using the calculated average value. Next, the pulse wave detection unit 13 performs a process of removing noise generated by the movement of the body or head, the change of facial expression, the change of the surrounding light environment, etc. from the acquired time-series change of the brightness value. The pulse wave detection unit 13 set the time-series change of the brightness value after processing as a pulse wave.

As a noise removal processing method, the following method can be mentioned as a desirable method. First, the pulse wave detection unit 13 frequency-converts a signal of time-series change in brightness value including noise for a set period (for example, 60 seconds) in units of windows for a time shorter than the set period (for example, 4 seconds). The pulse wave detection unit 13 calculates the frequency (frequency corresponding to the pulse component) at which the power is maximized for each window. Then, the pulse wave detection unit 13 extracts a signal of time-series change of the frequency corresponding to the pulse component by using the calculation result.

Next, the pulse wave detection unit 13 calculates statistical values (for example, average value, standard deviation, maximum value, minimum value, etc.) from the time-series change signal of the extracted frequency. The pulse wave detection unit uses the calculated statistical value to specify the frequency range in which the time-series change signal of that frequency is distributed. After that, the pulse wave detection unit 13 applies a bandpass filter that passes only the signals in the frequency range in which the time-series change signals are distributed, to the signal indicating the time-series change of the brightness value including the noise for the set period (60 seconds). As a result, noise unrelated to the pulse component is removed.

According to the noise removal processing method described above, the frequency value corresponding to the pulse calculated from the signal of the time-series change of the brightness value including noise includes an error. However, in the above-mentioned noise removal processing method, the error is suppressed in terms of the frequency range in which the time-series change signal is distributed by calculating the statistical value for the set period (60 seconds). Therefore, in the above-mentioned noise removal processing method, it is possible to effectively obtain a time-series change in the brightness value after noise removal, that is, a pulse wave.

In the present example embodiment, the second alertness estimation unit 14 determines whether or not the human 30 is awake according to the time-series change detected as the pulse wave by the pulse wave detection unit 13, and set the determination result as the second alertness. Specifically, the second alertness estimation unit 14 determines whether or not the human 30 is awake by using the neural network learned using the training data shown in FIG. 2. FIG. 2 is a diagram showing an example of training data used for learning the neural network used by the second alertness estimation unit in the example embodiment of the present invention.

Further, examples of the neural network used in the present example embodiment include a convolutional neural network and the like. In FIG. 2, when a time-series signal of a pulse wave from time T to time T+N (for example, 60 seconds) is input to the convolution neural network, the network is learned so that the input result matches the wakefulness (the second alertness).

The second alertness estimation unit 14 inputs a new pulse wave time-series signal other than the training data to the neural network. As a result, the neural network outputs "0" or "1" as the determination result of the second alertness. Then, the second alertness estimation unit 14 determines that the human 30 is awake when "1" is output and determines that the human 30 is asleep when "0" is output.

Figure 3:
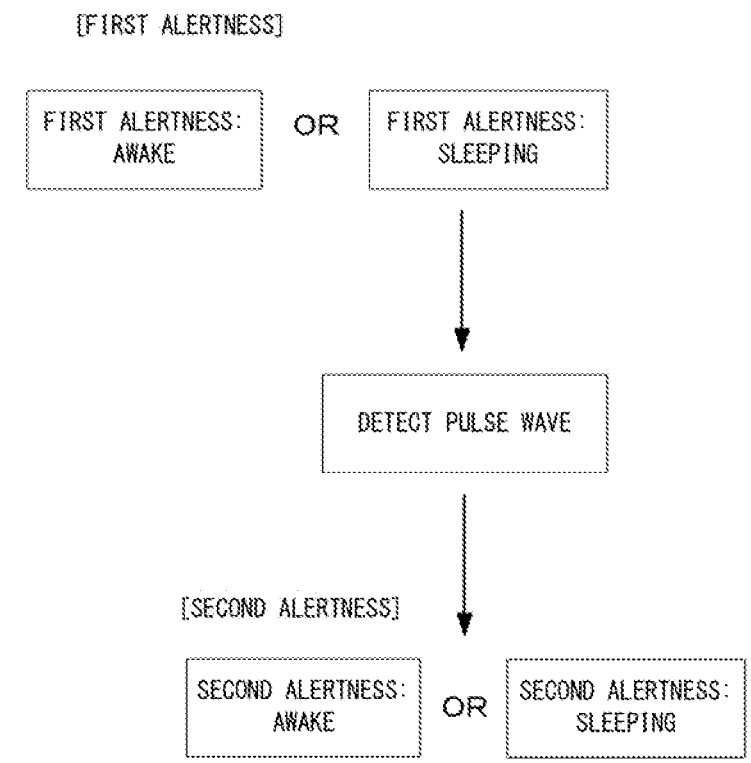
FIG. 3 is a diagram schematically showing a process performed by the alertness estimation apparatus according to the example embodiment of the present invention.

FIG. 3 is a diagram schematically showing a process performed by the alertness estimation apparatus according to the example embodiment of the present invention.

As shown in FIG. 3, the alertness estimation apparatus 10 detects the pulse wave only after it is determined to be "sleeping" by the first alertness estimated from the state of the eyes, and estimates the second alertness by using the detected pulse waves.

[Apparatus Operations]

Figure 4:
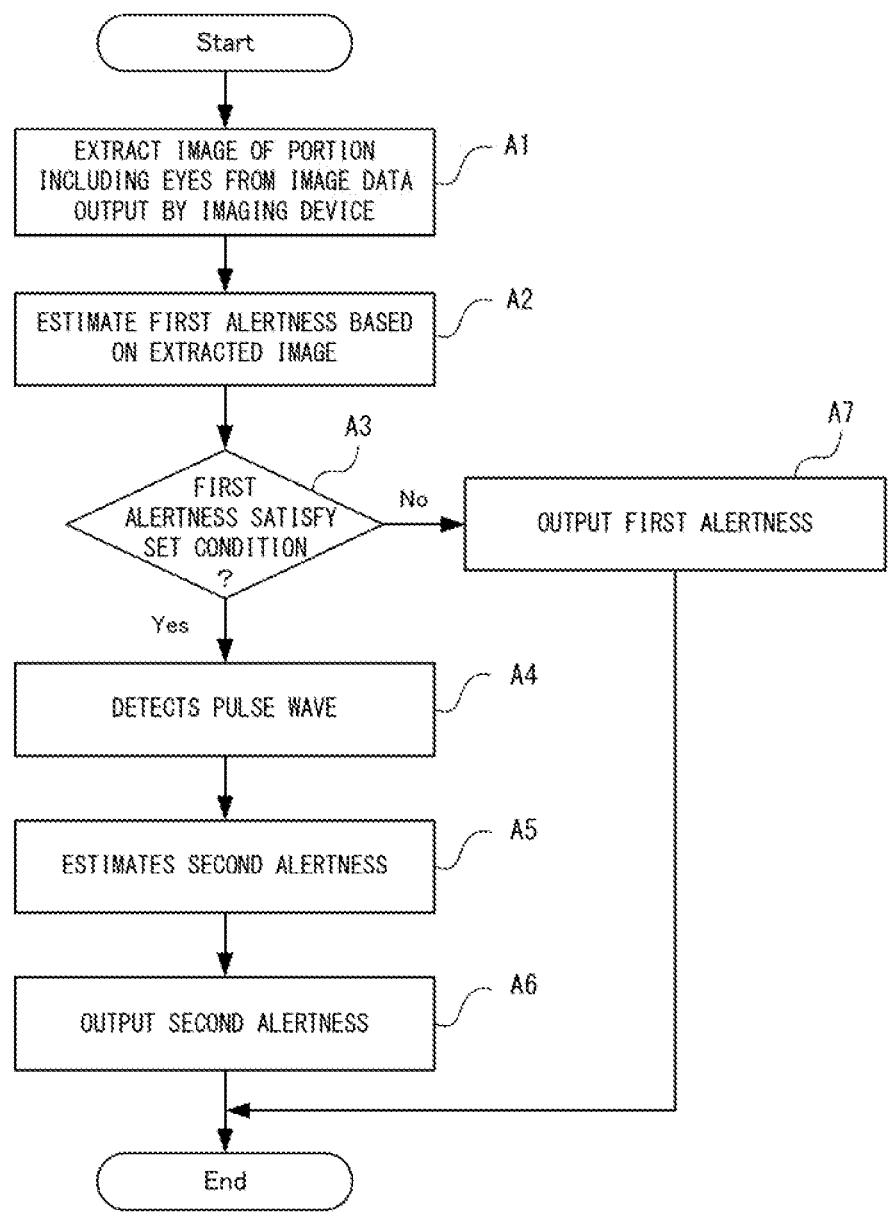
FIG. 4 is a flow diagram showing the operation of the alertness estimation apparatus according to the example embodiment of the present invention.

Next, the operations of the alertness estimation apparatus 10 according to the present example embodiment will be described using FIG. 4. FIG. 4 is a flow diagram showing the operation of the alertness estimation apparatus according to the example embodiment of the present invention. In the following description, FIG. 1 will be referred to as appropriate. Furthermore, in the present example embodiment, the alertness estimation method is canied out by causing the alertness estimation apparatus 10 to operate. Therefore, the following description of the operations of the alertness estimation 10 applies to the alertness estimation method according to the present example embodiment.

As shown in FIG. 4, first, the image extraction unit 11 receives the image data of the face image output by the imaging apparatus 20, and extracts the image of the portion including eyes from the received image data (step A1).

Next, the first alertness estimation unit 12 estimates the first alertness based on the image extracted in step A1 (step A2). Specifically, the first alertness estimation unit 12 detects the state of eyes from the image extracted in step A1, determines whether or not the human 30 is awake according to the detected state, and set the determination result as the first alertness.

Next, the pulse wave detection unit 13 determines whether or not the first alertness estimated in step A2 satisfies the set condition (step A3). Specifically, the pulse wave detection unit 13 determines whether or not the first alertness indicates that the human 30 is sleeping.

As a result of the determination in step A3, when the first alertness does not satisfy the set condition, that is, when the first alertness indicates that the human 30 is awake, the pulse wave detection unit 13 output the first alertness to an external device (step A7). Therefore, the first alertness is displayed on the screen of the external device. Examples of the external device include a display device, a terminal device, and the like.

On the other hand, as a result of the determination in step A3, when the first alertness satisfies the set condition, that is, when the first alertness indicates that the human 30 is sleeping, the pulse wave detection unit 13 detects the pulse wave of the human 30 from the face image of the image data acquired in step A1 (step A4).

Next, the second alertness estimation unit 14 estimates the second alertness of the human 30 based on the pulse wave detected in step A4 (step A5). Specifically, in the second example embodiment, the second alertness estimation unit 14 determines whether or not the human 30 is awakened according to the time-series change of the brightness value of the specific pixel detected by the pulse wave detection unit 13. The second alertness estimation unit 14 set the determination result as the second alertness.

After that, the second alertness estimation unit 14 outputs the second alertness estimated in step A5 to an external device (step A6). As a result, the second alertness is displayed on the screen of the external device.

Further, after the execution of step A6 or A7, step A1 is executed again. Steps A1 to A7 are repeatedly executed. As a result, the latest first alertness or second alertness is always displayed on the screen of the external device.

MODIFIED EXAMPLES

Hereinafter, modified examples 1 to 4 in the example embodiment will be described.

Modification 1:

In this modification 1, in the learning of the first alertness estimation model used in the first alertness estimation unit 12, a multi-step alertness to which a face image is given, for example, a five-step alertness (1: not sleepy at all, 0.75: slightly sleepy, 0.5: sleepy, 0.25: quite sleepy, 0.0: very sleepy) are used, as the first alertness that becomes the correct answer data. In the learning of the first alertness estimation model, the time when the eyes are closed, or the number of blinks are input as the state of the eyes, and the learning is performed so that the output matches the above correct answer data.

Further, in the present modification 1, the output of the first alertness estimation unit 12 is not a binary value (0 or 1) but a multi-value of 0 to 1. Therefore, the pulse wave detection unit 13 operates depending on whether or not the first alertness is below the threshold (condition). Further, when the first alertness is above the threshold, the pulse wave detection unit 13 does not operate, and when the first alertness is below the threshold, the pulse wave detection unit 13 operates.

Modification 2:

In this modification 2, in the learning of the second alertness estimation model used in the second alertness estimation unit 14, behavior information is used as the second alertness that becomes the correct answer data. The behavior information is obtained, for example, by asking the subject, which of the four stages (1.0: waking up, 0.66: light sleep, 0.33: normal sleep, 0.0: deep sleep) the behavior corresponds to.

Further, in the present modification 2, the output of the second alertness estimation unit 14 is not a binary value (0 or 1) but a multi-value of 0 to 1. Further, in the present modification 2, the multi-valued output may be converted into a binary value (awakening or sleeping) by the second alertness estimation unit 14, and then output.

Modification 3:

In this modification 3, the second alertness estimation unit 14 determines whether or not the human 30 is awake using a learning model, and the determination result as the second alertness. The learning model is constructed by machine learning the relationship between a brain activity of the human 30 and the pulse wave of the human 30.

In the third modification, the learning model can be constructed, for example, by learning the convolutional neural network using the training data shown in FIG. 5. FIG. 5 is a diagram showing an example of training data used in the modified example 3 according to the present example embodiment.

In the example of FIG. 5, the combination data of the pulse wave signal and the label indicating the behavior (REM sleep, non-REM sleep or awakening) of the brain of the human 30 at that time is used as the training data. In this case, the second alertness estimation unit 14 estimates the second alertness by applying the time-series signal of the pulse wave to the learning model.

Effects in the Example Embodiment

As described above, according to the present example embodiment, the second alertness is estimated by the pulse wave only after the first alertness estimated from the state of eyes is determined to be "sleeping". Therefore, the increase in the processing load in the alertness estimation apparatus 10 is suppressed. Further, since the pulse wave is detected from the face image as in the first alertness, it is not necessary to prepare a new sensor for detecting the pulse wave, so that the increase in the introduction cost is suppressed.

[Program]

It is sufficient for the program according to the present example embodiment to be a program that causes a computer to execute steps A1 to A7 shown in FIG. 4. The alertness estimation apparatus and the alertness estimation method according to the present example embodiment can be realized by installing this program in the computer and executing this program. In this case, a processor of the computer functions as the image extraction unit 11, the first alertness estimation unit 12, the pulse wave detection unit 13, and the second alertness estimation unit 14, and performs processing.

Furthermore, the program according to the present example embodiment may be executed by a computer system constructed with a plurality of computers. In this case, for example, each computer may function as one of the image extraction unit 11, the first alertness estimation unit 12, the pulse wave detection unit 13, and the second alertness estimation unit 14.

Figure 6:
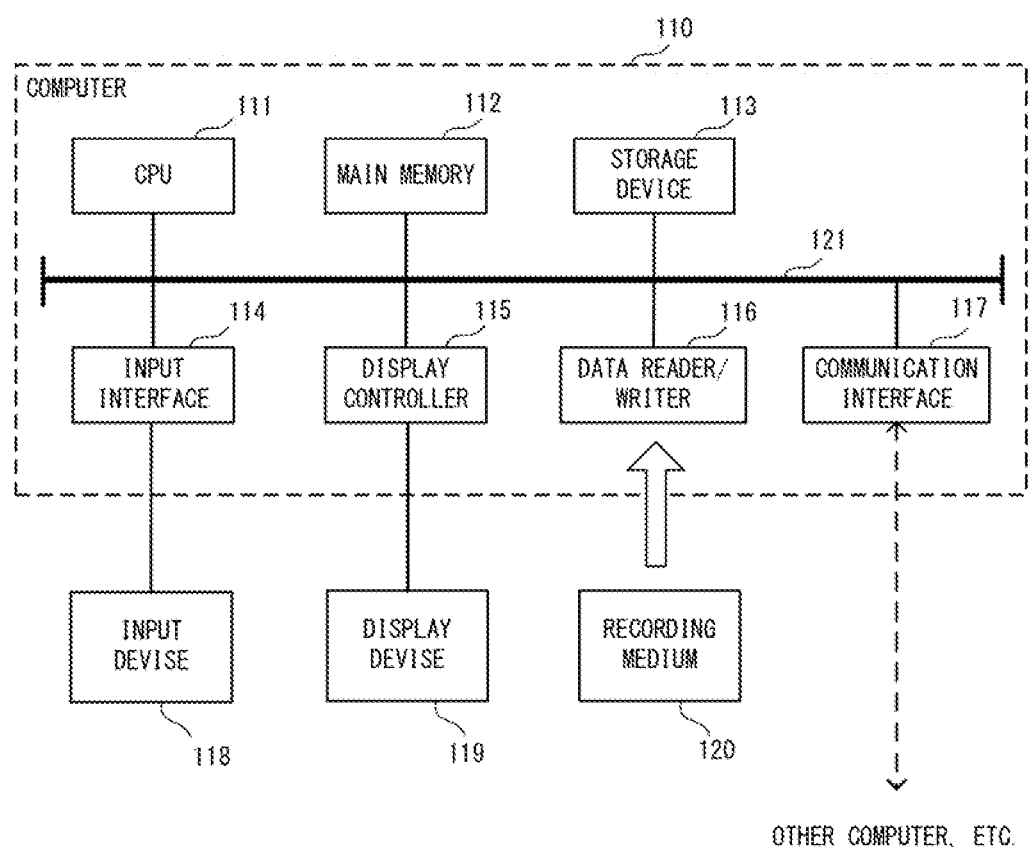
FIG. 6 is a block diagram showing an example of a computer that realizes the alertness estimation apparatus according to the example embodiment of the present invention.

Here, using FIG. 10, the following describes a computer that realizes the alertness estimation apparatus 10 by executing the program according to the present example embodiment FIG. 6 is a block diagram showing an example of a computer that realizes the alertness estimation apparatus according to the example embodiment of the present invention.

As shown in FIG. 6, a computer 110 includes a CPU (Central Processing Unit) 111, a main memory 112, a storage device 113, an input interface 114, a display controller 115, a data reader/writer 116, and a communication interface 117. These components are connected in such a manner that they can perform data communication with one another via a bus 121. Note that the computer 110 may include a GPU (Graphics Processing Unit) or an FPGA (Field-Programmable Gate Array) in addition to the CPU 111, or in place of the CPU 111.

The CPU 111 carries out various types of calculation by deploying the program (codes) according to the present example embodiment stored in the storage device 113 to the main memory 112, and executing the codes in a predetermined order. The main memory 112 is typically a volatile storage device, such as a DRAM (dynamic random-access memory). Also, the program according to the present example embodiment is provided in a state where it is stored in a computer-readable recording medium 120. Note that the program according to the present example embodiment may be distributed over the Internet connected via the communication interface 117.

Also, specific examples of the storage device 113 include a hard disk drive and a semiconductor storage device, such as a flash memory. The input interface 114 mediates data transmission between the CPU 111 and an input apparatus 118, such as a keyboard and a mouse. The display controller 115 is connected to a display apparatus 119, and controls display on the display apparatus 119.

The data reader/writer 116 mediates data transmission between the CPU 111 and the recording medium 120, reads out the program from the recording medium 120, and writes the result of processing in the computer 110 to the recording medium 120. The communication interface 117 mediates data transmission between the CPU 111 and another computer.

Specific examples of the recording medium 120 include a general-purpose semiconductor storage device such as CF (CompactFlash®) and SD (Secure Digital), a magnetic recording medium such as a flexible disk; and an optical recording medium such as a CD-ROM (Compact Disk Read Only Memory).

Note that the alertness estimation apparatus 10 according to the present example embodiment can also be realized by using items of hardware that respectively correspond to the components, rather than the computer in which the program is installed. Furthermore, a part of the alertness estimation apparatus 10 may be realized by the program, and the remaining part of the alertness estimation apparatus 10 may be realized by hardware.

A part or an entirety of the above-described example embodiment can be represented by (Supplementary Note 1) to (Supplementary Note 21) described below, but is not limited to the description below.

(Supplementary Note 1)
An alertness estimation apparatus, including:
an image extraction unit that configured to extract an image of a portion including eyes from an image data of a face image of a human;
a first alertness estimation unit that configured to estimate a first alertness based on the extracted image;
a pulse wave detection unit that configured to determine whether or not the estimated first alertness satisfies a set condition, and detect a pulse wave of the human from the face image, when the first alertness satisfies the set condition; and
a second alertness estimation unit that configured to estimate a second alertness of the human based on the detected pulse wave.

(Supplementary Note 2)
The alertness estimation apparatus according to Supplementary Note 1, wherein
the first alertness estimation unit detects a state of eyes from the extracted image, determines whether or not the human is awake according to the detected state, and set the determination result as the first alertness, and
when the first alert estimation unit determines that the human is not awake, the pulse wave detection unit determines that the first alertness satisfies the set condition, and then detect the pulse wave of the human from the face image.

(Supplementary Note 3)
The alertness estimation apparatus according to Supplementary Note 2, wherein
the first alertness estimation unit determines whether or not the human is awake by using a learning model, and the learning model is constructed by machine learning a relationship between a state of eyes shown in an image and a wakefulness of a human.

(Supplementary Note 4)
The alertness estimation apparatus according to Supplementary Note 1 or 2, wherein
the pulse wave detection unit detect the pulse wave of the human by detecting time series change of a brightness value of a specific pixel from the face image,
the second alertness estimation unit determines whether or not the human is awake according to the detected time series change and set the determination result as the second alertness.

(Supplementary Note 5)
The alertness estimation apparatus according to Supplementary Note 4, wherein
the second alertness estimation unit determines whether or not the human is awake by using a learning model, and the learning model is constructed by machine learning a relationship between a behavior of a human and a plus wave of a human (Supplementary Note 6)
The alertness estimation apparatus according to Supplementary Note 4, wherein
the second alertness estimation unit determines whether or not the human is awake by using a learning model, and the learning model is constructed by machine learning a relationship between a brain activity of a human and a plus wave of a human (Supplementary Note 7)
The alertness estimation apparatus according to any of Supplementary Notes 1 to 6, wherein
the second alertness estimation unit estimates the second alertness after removing noise contained in the pulse wave according to a heart rate estimated from the pulse wave.

(Supplementary Note 8)
An alertness estimation method, including:
(a) a step of extracting an image of a portion including eyes from an image data of a face image of a human;
(b) a step of estimating a first alertness based on the extracted image;
(c) a step of determining whether or not the estimated first alertness satisfies a set condition, and detecting a pulse wave of the human from the face image, when the first alertness satisfies the set condition; and
(d) a step of estimating a second alertness of the human based on the detected pulse wave.

(Supplementary Note 9)
The alertness estimation method according to Supplementary Note 8, wherein
in the (b) step, detecting a state of eyes from the extracted image, determining whether or not the human is awake according to the detected state, and setting the determination result as the first alertness, and
when it is determined in the (b) step that the human is not awake, in the (c) step, determining the first alertness satisfies the set condition, and then detecting the pulse wave of the human from the face image.

(Supplementary Note 10)

The alertness estimation method according to Supplementary Note 9, wherein in the (b) step, determining whether or not the human is awake by using a learning model, and the learning model is constructed by machine learning a relationship between a state of eyes shown in an image and a wakefulness of a human.

(Supplementary Note 11)

The alertness estimation method according to Supplementary Note 8 or 9, wherein in the (c) step, detecting the pulse wave of the human by detecting time series change of a brightness value of a specific pixel from the face image, in the (d) step, determining whether or not the human is awake according to the detected time series change and setting the determination result as the second alertness.

(Supplementary Note 12)

The alertness estimation method according to Supplementary Note 11, wherein in the (d) step, determining whether or not the human is awake by using a learning model, and the learning model is constructed by machine learning a relationship between a behavior of a human and a plus wave of a human.

(Supplementary Note 13)

The alertness estimation method according to Supplementary Note 12, wherein in the (d) step, determining whether or not the human is awake by using a learning model, and the learning model is constructed by machine learning a relationship between a brain activity of a human and a plus wave of a human (Supplementary Note 14)

The alertness estimation method according to any of Supplementary Notes 8 to 13, wherein in the (d) step, estimating the second alertness after removing noise contained in the pulse wave according to a heart rate estimated from the pulse wave.

(Supplementary Note 15)

A computer-readable recording medium in which a program is recorded, the program including instructions that causes a computer to cany out:

(a) a step of extracting an image of a portion including eyes from an image data of a face image of a human;

(b) a step of estimating a first alertness based on the extracted image;

(c) a step of determining whether or not the estimated first alertness satisfies a set condition, and detecting a pulse wave of the human from the face image, when the first alertness satisfies the set condition; and (d) a step of estimating a second alertness of the human based on the detected pulse wave.

(Supplementary Note 16)

The computer-readable recording medium according to Supplementary Note 15, wherein in the (b) step, detecting a state of eyes from the extracted image, determining whether or not the human is awake according to the detected state, and setting the determination result as the first alertness, and when it is determined in the (b) step that the human is not awake, in the (c) step, determining the first alertness satisfies the set condition, and then detecting the pulse wave of the human from the face image.

(Supplementary Note 17)

The computer-readable recording medium according to Supplementary Note 16, wherein in the (b) step, determining whether or not the human is awake by using a learning model, and the learning model is constructed by machine learning a relationship between a state of eyes shown in an image and a wakefulness of a human.

(Supplementary Note 18)

The computer-readable recording medium according to Supplementary Note 15 or 16, wherein in the (c) step, detecting the pulse wave of the human by detecting time series change of a brightness value of a specific pixel from the face image, in the (d) step, determining whether or not the human is awake according to the detected time series change and setting the determination result as the second alertness.

(Supplementary Note 19)

The computer-readable recording medium according to Supplementary Note 18, wherein in the (d) step, determining whether or not the human is awake by using a learning model, and the learning model is constructed by machine learning a relationship between a behavior of a human and a plus wave of a human.

(Supplementary Note 20)

The computer-readable recording medium according to Supplementary Note 18, wherein in the (d) step, determining whether or not the human is awake by using a learning model, and the learning model is constructed by machine learning a relationship between a brain activity of a human and a plus wave of a human.

(Supplementary Note 21)

The computer-readable recording medium according to any of Supplementary Notes 15 to 20, wherein in the (d) step, estimating the second alertness after removing noise contained in the pulse wave according to a heart rate estimated from the pulse wave.

Although the invention of the present application has been described above with reference to the example embodiment, the invention of the present application is not limited to the above-described example embodiment. Various changes that can be understood by a person skilled in the art within the scope of the invention of the present application can be made to the configuration and the details of the invention of the present application.

INDUSTRIAL APPLICABILITY

As described above, according to the present invention, it is possible to detect a wakefulness of human without increasing the introduction cost and the processing load. The present invention is useful for systems in which detection of the wakefulness of humans is required, for example, a vehicle driving support system, a computer system for business use, and the like.

REFERENCE SIGNS LIST 10 alertness estimation apparatus
11 image extraction unit
12 first alertness estimation unit
13 pulse wave detection unit
14 second alertness estimation unit
20 imaging device
30 human 110 computer
111 CPU
112 main memory
113 storage device
114 input interface
115 display controller
116 data reader/writer
117 communication interface
118 input apparatus
119 display apparatus
120 recording medium
121 bus

The invention claimed is:

1. An alertness estimation apparatus comprising:
at least one processor; and
at least one memory storing instructions executable by the at least one processor to:
extract an eyes image including eyes of a person from a face image including a face of the person;
calculate a degree of opening and closing of eyelids of the eyes of the person in the eyes image;
calculate a length of time during which the eyelids are closed from a time-series change in the degree of opening and closing of the eyelids;
determine that the person is awake when the length of time is equal to or less than a threshold value;
determine that the person is sleeping when the length of time exceeds the threshold value;
set a first alertness level to one when the person has been determined to be awake;
set the first alertness level to zero when the person has been determined to be sleeping;
detect a pulse wave of the human person from the face image when the first alertness level has been set to zero; and
estimate a second alertness level of the person based on the pulse wave.

2. The alertness estimation apparatus according to claim 1, wherein
the pulse wave of the person is detected by detecting a time-series change of a brightness value of a specific pixel in the face image,
the instructions are executable by the at least one processor to again determine whether the person is awake or sleeping, according to the time-series change of the brightness of the specific pixel,
the second alertness level is set to one when the person has been determined to be awake according to the time-series change of the brightness of the specific pixel, and
the second alertness level is set to zero when the person has been determined to be sleeping according to the time-series change of the brightness of the specific pixel.

3. The alertness estimation apparatus according to claim 2, wherein
whether the human is awake or sleep is determined according to the time-series change of the brightness of the specific pixel by using a learning model constructed by machine learning a relationship between a human behavior human pulse wave.

4. The alertness estimation apparatus according to claim 2, wherein
whether the human is awake or sleep is determined according to the time-series change of the brightness of the specific pixel by using a learning model constructed by machine learning a relationship between human brain activity and human pulse.

5. The alertness estimation apparatus according to claim 1, wherein
the instructions are executable by the at least one processor to further remove noise contained in the pulse wave according to a heart rate estimated from the pulse wave, and
the second alertness is estimated after the noise contained in the pulse wave has been removed.

6. An alertness estimation method comprising:
extracting, by a processor, an eyes image including eyes of a person from a face image including a face of the person;
calculating, by the processor, a degree of opening and closing of eyelids of the eyes of the person in the eyes image;
calculating, by the processor, a length of time during which the eyelids are closed from a time-series change in the degree of opening and closing of the eyelids;
determining, by the processor, that the person is awake when the length of time is equal to or less than a threshold value;
determining, by the processor, that the person is sleeping when the length of time exceeds the threshold value;
setting, by the processor, a first alertness level to one when the person has been determined to be awake;
setting, by the processor, the first alertness level to zero when the person has been determined to be sleeping;
detecting, by the processor, a pulse wave of the person from the face image when the first alertness level has been set to zero; and
estimating, by the processor, a second alertness level of the person based on the pulse wave.

7. The alertness estimation method according to claim 6, wherein
the pulse wave of the person is detected by detecting a time-series change of a brightness value of a specific pixel in the face image,
the method further comprises again determining, by the processor, whether the person is awake or sleeping, according to the time-series change of the brightness of the specific pixel,
the second alertness level is set to one when the person has been determined to be awake according to the time-series change of the brightness of the specific pixel, and
the second alertness level is set to zero when the person has been determined to be sleeping according to the time-series change of the brightness of the specific pixel.

8. The alertness estimation method according to claim 7, wherein
whether the human is awake or sleep is determined according to the time-series change of the brightness of the specific pixel by using a learning model constructed by machine learning a relationship between a human behavior human pulse wave.

9. The alertness estimation method according to claim 7, wherein
whether the human is awake or sleep is determined according to the time-series change of the brightness of the specific pixel by using a learning model constructed by machine learning a relationship between human brain activity and human pulse.

10. The alertness estimation method according to claim 6, wherein the method further comprises removing, by the processor, noise contained in the pulse wave according to a heart rate estimated from the pulse wave, and the second alertness is estimated after the noise contained in the pulse wave has been removed.

11. A non-transitory computer-readable recording medium storing a program executable by a computer to carry out:

extracting an eyes image including eyes of a person from a face image including a face of the person;

calculating a degree of opening and closing of eyelids of the eyes of the person in the eyes image;

calculating a length of time during which the eyelids are closed from a time-series change in the degree of opening and closing of the eyelids;

determining that the person is awake when the length of time is equal to or less than a threshold value;

determining that the person is sleeping when the length of time exceeds the threshold value;

setting a first alertness level to one when the person has been determined to be awake;

setting the first alertness level to zero when the person has been determined to be sleeping;

detecting a pulse wave of the person from the face image when the first alertness level has been set to zero; and estimating a second alertness level of the person based on the pulse wave.

12. The non-transitory computer-readable recording medium according to claim 11, wherein the pulse wave of the person is detected by detecting a time-series change of a brightness value of a specific pixel in the face image, the program is executable by the computer to further carry out again determining whether the person is awake or sleeping, according to the time-series change of the brightness of the specific pixel, the second alertness level is set to one when the person has been determined to be awake according to the time-series change of the brightness of the specific pixel, and the second alertness level is set to zero when the person has been determined to be sleeping according to the time-series change of the brightness of the specific pixel.

13. The non-transitory computer-readable recording medium according to claim 12, wherein whether the human is awake or sleep is determined according to the time-series change of the brightness of the specific pixel by using a learning model constructed by machine learning a relationship between a human behavior human pulse wave.

14. The non-transitory computer-readable recording medium according to claim 12, wherein whether the human is awake or sleep is determined according to the time-series change of the brightness of the specific pixel by using a learning model constructed by machine learning a relationship between human brain activity and human pulse.

* * * * *